(12) United States Patent
Strgar

(10) Patent No.: US 10,195,169 B2
(45) Date of Patent: *Feb. 5, 2019

(54) SYSTEMS AND METHODS FOR BIO-MATCHING GELS, CREAMS AND LOTIONS

(71) Applicant: Good Clean Love, Inc., Eugene, OR (US)

(72) Inventor: Wendy Strgar, Eugene, OR (US)

(73) Assignee: GOOD CLEAN LOVE, INC., Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,645

(22) Filed: Aug. 30, 2017

(65) Prior Publication Data

US 2017/0360728 A1    Dec. 21, 2017

Related U.S. Application Data

(63) Continuation-in-part of application No. 15/294,340, filed on Oct. 14, 2016, now abandoned, which is a continuation of application No. 14/636,035, filed on Mar. 2, 2015, now Pat. No. 9,470,676.

(60) Provisional application No. 62/094,769, filed on Dec. 19, 2014.

(51) Int. Cl.
| | | |
|---|---|---|
| A61K 31/191 | (2006.01) | |
| A61P 15/02 | (2006.01) | |
| A61K 47/36 | (2006.01) | |
| A61K 9/06 | (2006.01) | |
| G01N 33/50 | (2006.01) | |
| A61K 9/00 | (2006.01) | |

(52) U.S. Cl.
CPC .............. *A61K 31/191* (2013.01); *A61K 9/00* (2013.01); *A61K 9/0034* (2013.01); *A61K 9/06* (2013.01); *A61K 47/36* (2013.01); *G01N 33/50* (2013.01)

(58) Field of Classification Search
CPC .................................................... A61K 31/191
See application file for complete search history.

(56) References Cited

U.S. PATENT DOCUMENTS

| | | | |
|---|---|---|---|
| 5,466,463 A | 11/1995 | Ford | |
| 5,765,579 A | 6/1998 | Heiler et al. | |
| 5,778,886 A | 7/1998 | Shihata | |
| 6,045,786 A | 4/2000 | Cone et al. | |
| 6,892,732 B2 | 5/2005 | Wang et al. | |
| 8,367,098 B2 | 2/2013 | Maguire et al. | |
| 9,470,676 B2 * | 10/2016 | Strgar | G01N 33/50 |
| 2004/0132690 A1 | 7/2004 | Carmella et al. | |
| 2009/0105314 A1 | 4/2009 | Ii et al. | |
| 2012/0195961 A1 | 8/2012 | Kritikou et al. | |
| 2013/0039944 A1 | 2/2013 | Iadonato et al. | |

FOREIGN PATENT DOCUMENTS

| | | |
|---|---|---|
| CN | 1113150 A | 12/1995 |
| CN | 101559036 A | 10/2009 |
| CN | 101773513 A | 7/2010 |
| CN | 102266283 A | 12/2011 |
| CN | 102512338 A | 6/2012 |
| EP | 1582186 A1 | 10/2005 |
| EP | 2018872 A1 | 1/2009 |
| JP | 3264520 A | 11/1991 |
| JP | 10001430 A | 1/1998 |
| KR | 20090054777 A | 6/2009 |
| WO | 0195951 A1 | 12/2001 |
| WO | 2006075236 A1 | 7/2006 |

OTHER PUBLICATIONS

Gynofit Gel with Lactic acid from Tentan AG, 2010.*
Aroutcheva et al., Am. J. Obstet Gynecol, 2001, 185(2): 375-379.*
Berge et al., Journal of Pharmaceutical Sciences, 1977, 66(1): 1-19.*
Aroutcheva, MD, Alla et al., "Defense factors of vaginal lactobacilli", American Journal of Obstetrics and Gynecology, vol. 185, No. 2, Aug. 2001, pp. 375-379.
Balance Activ Vaginal Gel product information, http://www.expresschemist.co.uk, accessed on Mar. 4, 2013, 2 pages.
Berge, Stephen M. et al., "Pharmaceutical Salts" review article, Journal of Pharmaceutical Sciences, vol. 66, No. 1, Jan. 1977, 18 pages.
Gynofit Gel with Lactic acid from Tentan AG, 2010, 2 pages.
Gynofit lactic acid vaginal gel product information, http://www.efarma.lt, accessed on Mar. 4, 2013, 3 pages.
Manjakani Plus Feminine Wash with Kacip Fatimah product information, https://www.herbsforlove.com, accessed on Mar. 4, 2013, 2 pages.
Oench et al., "Microbicide excipients can greatly increase susceptibility to genital herpes transmission in the mouse", BMC Infectious Diseases, vol. 10 No. 331, 2010, 9 pages.
Natural ecological Lubricant, Organic Products Without Intermediaries product information, http://www.productosecologicossinintermediarios.es, accessed on Mar. 4, 2013, 3 pages.
Pre-Seed Vaginal Lubricant product information, https://www.amazon.co.uk, accessed on Sep. 20, 2013, 6 pages.
Vegan Spermicide Alternative product information, https://veganlove.com, made aware of on Mar. 4, 2013, 7 pages.
Yes Intimate Lubricants product information, https://www.thenaturalskincarecompany.co.uk, accessed on Sep. 20, 3013, 4 pages.

* cited by examiner

*Primary Examiner* — Rei Tsang Shiao

(57) ABSTRACT

A method of bio-matching a topical gel, cream or lotion includes selecting a vagina of a living body, identifying a secretion of the selected vagina, identifying a composition of the identified secretion, and formulating the topical gel to match the identified composition of the identified secretion.

16 Claims, 5 Drawing Sheets

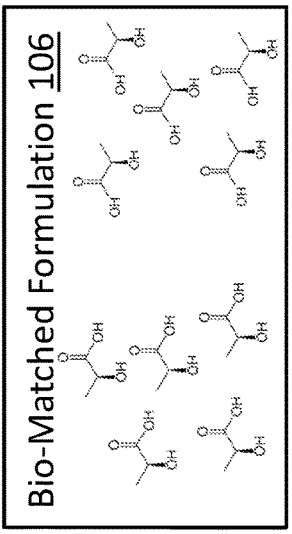
Fig. 6 Bio-Matched Formulation 106
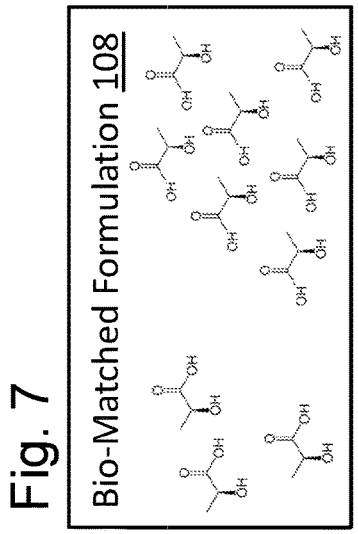
Fig. 7 Bio-Matched Formulation 108
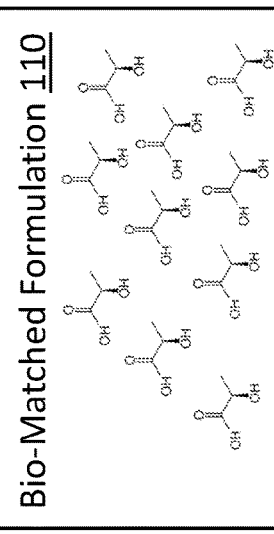
Fig. 8 Bio-Matched Formulation 110
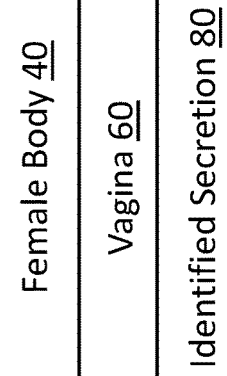
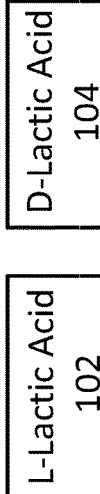
Fig. 5
Female Body 40
Vagina 60
Identified Secretion 80
Composition 100
L-Lactic Acid 102
D-Lactic Acid 104

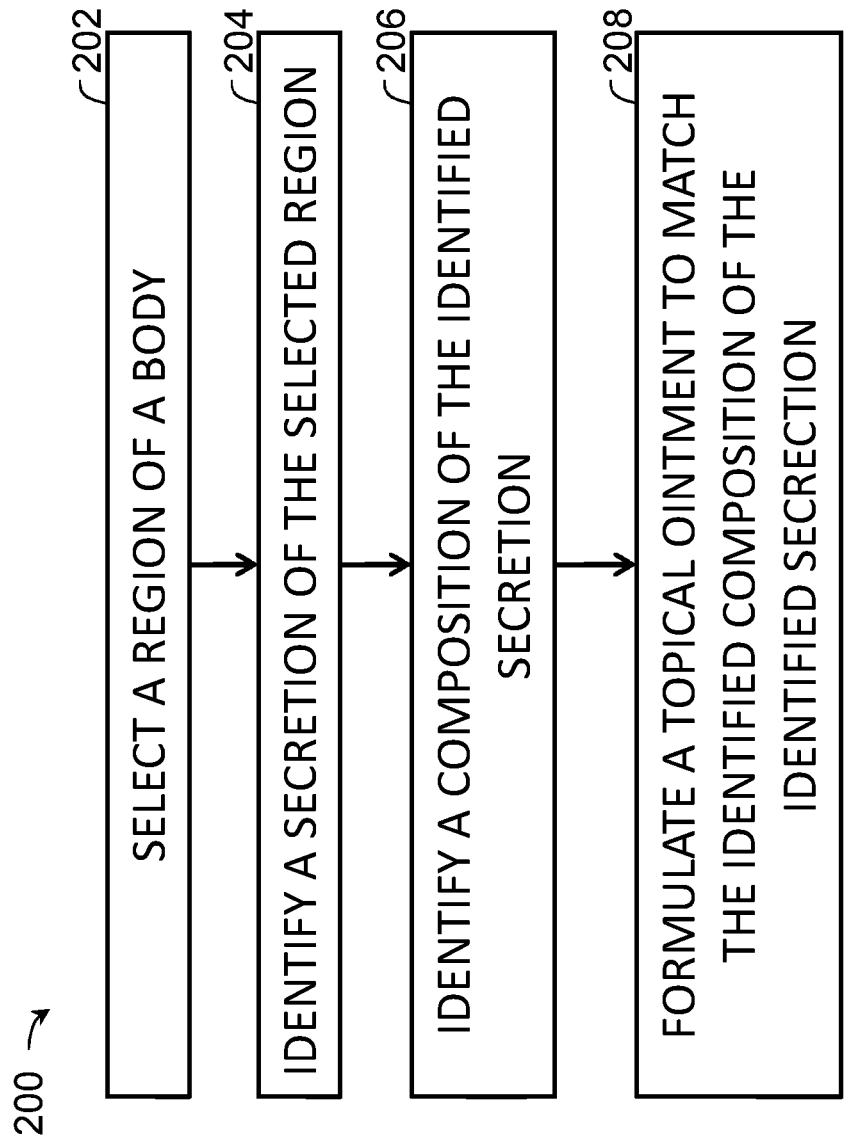

SYSTEMS AND METHODS FOR BIO-MATCHING GELS, CREAMS AND LOTIONS

CROSS-REFERENCE TO RELATED APPLICATIONS

This application is a continuation in part of U.S. patent application Ser. No. 15/294,340, which is a continuation of U.S. patent application Ser. No. 14/636,035, filed Mar. 2, 2015, which issued as U.S. Pat. No. 9,470,676, which application is based upon and claims the benefit under 35 U.S.C. § 119(e) of U.S. Provisional Patent Application Ser. No. 62/094,769, filed Dec. 19, 2014, which is incorporated herein by reference in its entirety for all purposes.

FIELD

The general field of invention relates to systems and methods for bio-matching gels, creams and other suitable formulations to a living body, particularly a human body.

INTRODUCTION

Portions of a human body typically secrete or produce various substances that may provide various benefits. For example, a mouth typically secretes saliva, which aids in digestion and provides lubrication for portions of the mouth. Microflora (e.g., including lactobacilli) of a vagina typically produce lactic acid, which may protect the vagina from various diseases, such as bacterial vaginosis (BV).

Often bodily secretions are supplemented with various over the counter (OTC) and/or prescription secretion supplements. For example, a person may supplement secretions produced by their lips with an OTC lip balm. In another example, a female may supplement secretions produced by her vagina with an OTC or prescription personal lubricant.

However, pre-existing secretion supplements often include components that were presumed to be safe but that actually harm the portion of the body being supplemented. For example, pre-existing personal or vaginal lubricants, such as K-Y® jelly, often include components that may damage the vagina and/or may make the vagina more susceptible to disease. For example, pre-existing vaginal lubricants are often formulated to have pH values of 6-7, which are much higher than the acidic pH of the healthy vagina, which has a pH of around 3.5. This may allow sexually transmitted diseases (STDs) to occur and may lead to other diseases as well, such as BV.

Similarly, Pre-seed®, a pre-existing pro-conception lubricant, also does not have an acidic pH but rather has a somewhat alkaline pH of 7.29. This high pH alkalizes the vagina to promote the life of sperm, but by doing so may make the vagina more susceptible to HIV and other STD pathogens.

Further, pre-existing personal lubricants are formulated with an osmolality much greater than an osmolality of a typical vagina. Using such a personal lubricant may result in the cells of the vagina releasing fluid to dilute the personal lubricant, which may result in death of the cells, damage to the vagina, and/or subsequent dryness of the vagina.

Moreover, pre-existing vaginal products commonly include other various ingredients which are harmful to the vagina. For example, these vaginal products typically include detergents and surface-active agents, glycerol (glycerine) and other humectant/solvent excipients, and/or preservatives which typically include chlorhexidine and/or ethylenediaminetetraacetic acid (EDTA), among others. Detergents and surface-active ingredients are harmful because they are markedly toxic to mucosal epithelia, including that of the vagina. Such detergents and surface-active ingredients may include nonoxynol-9 and similar detergents, and glycerol monolaurate (GML). Glycerol (glycerine) and other humectant/solvent excipients are harmful because they increase vaginal susceptibility to disease. For example, Moench et al. (BMC Infectious Diseases 2010, 10:331) reported that the following excipients markedly increased susceptibility to HSV-2 after a single exposure: 5% glycerol monolaurate (GML) formulated in K-Y® Warming Jelly, 5% GML as a colloidal suspension in phosphate buffered saline, K-Y Warming Jelly alone, and both of its humectant/solvent ingredients (neat propylene glycol and neat polyethylene glycol (PEG-8)).

SUMMARY

The present invention provides systems and methods for bio-matching formulations (e.g., gels, creams, etc.) to a particular region (or part) of a living body, such as that of a human or other animal. Formulations and methods of formulating thereof may provide compositions that both supplement secretions of the particular region of the living body and promote the health of the particular region. In one embodiment, a method of bio-matching a topical gel is provided. The method may comprise selecting a vagina of a living female body; identifying a secretion of the selected vagina; identifying a composition of the identified secretion; and formulating the topical gel to match the identified composition of the identified secretion. The matching includes using a preselected type and quantity of lactic acid, and formulating to a preselected pH and salt composition.

In another embodiment, a topical gel for human use is provided. The gel may comprise a formulation matched to a composition of a particular part of a human body. The formulation may include lactic acid, and the particular part may be a vagina.

In another embodiment, a topical gel for human use may comprise a formulation including lactic acid having a racemic index in a range of about 50% L/50% D. The formulation may be matched to a composition (or chemistry thereof) of a particular part of a human body.

In another embodiment, a vaginal lubricant is provided. The lubricant may comprise a formulation including lactic acid having a racemic index that is bio-matched but not bio-identical to a racemic index of natural lubricants in a generally healthy vagina.

BRIEF DESCRIPTION OF THE DRAWINGS

FIG. 5 is a block diagram of a female body, which schematically depicts a composition of an identified secretion of a vagina.

FIG. 6 is a block diagram schematically depicting a first formulation bio-matched to the composition of FIG. 5.

FIG. 7 is a block diagram schematically depicting a second formulation bio-matched but not bio-identical to the composition of FIG. 5.

FIG. 8 is a block diagram schematically depicting a third formulation bio-matched but not bio-identical to the composition of FIG. 5.

FIG. 11 is a flowchart depicting a method of bio-matching a topical gel to a living body.

DETAILED DESCRIPTION

Figure 1:
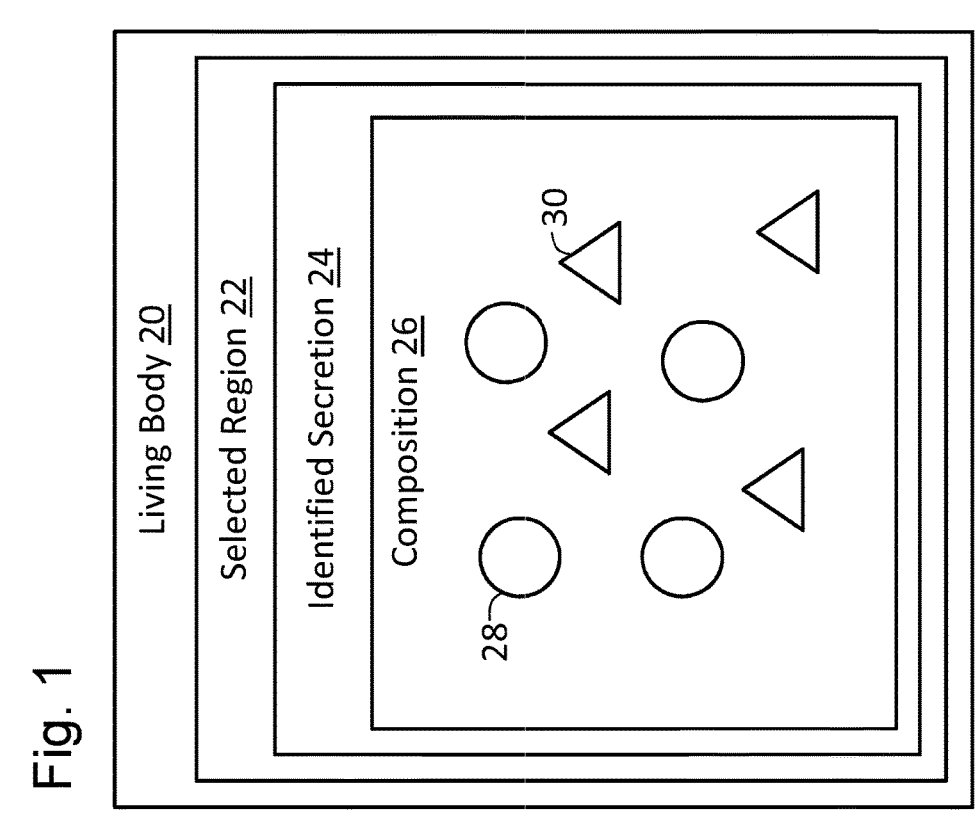
FIG. 1 is a block diagram schematically depicting a composition of an identified secretion of a selected region of a living body.

FIG. 1 shows a living body 20, which may be that of a human or other animal. In some embodiments, body 20 may be a body of a plant. Body 20 may have one or more regions (or components), such an eye region, an ear region, a vaginal region, a mouth region, and a rectal region among others. A selected region 22 of the one or more regions may produce one or more secretions for one or more purposes (e.g., to produce one or more desired effects). For example, a mouth region may produce saliva to lubricate the mouth region.

The one or more secretions of the selected region may include an identified secretion 24. For example, identified secretion 24 may be a secretion that has been identified as contributing substantially to producing the desired effect (e.g., mouth lubrication, digestion, tartar control, etc.) and/or to promoting the health of the region.

As shown in FIG. 1, identified secretion 24 may include composition 26, which may include one or more chemical compositions, ionic compositions, molecular structures, and/or molecular compositions. For example, the composition may include a first portion of a first type of composition 28, and a second portion of a second type of composition 30. FIG. 1 shows the first and second portions including equal amounts of compositions 28 and 30. In some embodiments, composition 26 may include more than two types of different compositions, and/or may include various ratios of portions thereof.

In some embodiments, body 20 may be a generally healthy body, region 22 may be a generally healthy region, and/or secretion 24 (and/or one or more components of composition 26) may be identified as contributing to the health of region 22 and/or body 20. For example, the composition of region 22 may correspond to a generally healthy composition (e.g., associated with flora of a generally healthy vagina). For example, one or more components of composition 26 or characteristics or properties thereof may be associated with (or present in) generally healthy vagina secretions.

Figure 2:
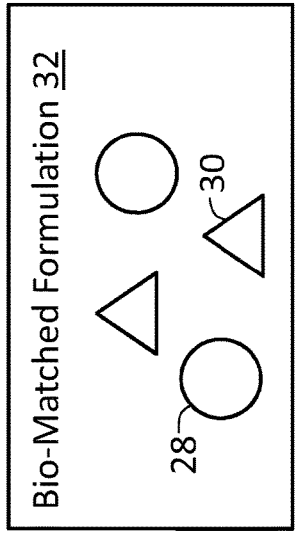
FIG. 2 is a block diagram schematically depicting a first formulation bio-matched to the composition of FIG. 1.

FIG. 2 shows a first formulation 32 that is bio-matched to body 20. For example, formulation 32 may be described as being bio-matched to composition 26. As shown, bio-matched formulation 32 includes a ratio of composition 28 to composition 30 that is equal to the ratio of composition 28 to composition 30 of secretion 24 in FIG. 1.

Figure 3:
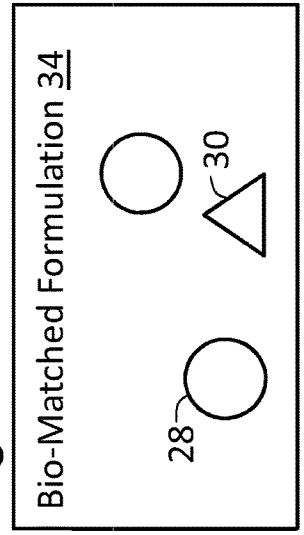
FIG. 3 is a block diagram schematically depicting a second formulation bio-matched but not bio-identical to the composition of FIG. 1.
Figure 4:
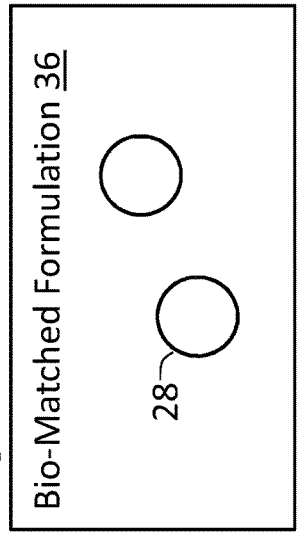
FIG. 4 is a block diagram schematically depicting a third formulation bio-matched but not bio-identical to the composition of FIG. 1.

In some embodiments, formulations bio-matched to secretion 24 may have ratios that are not equal to the ratio of compositions of secretion 24. For example, FIG. 3 shows a formulation 34 having a higher ratio of composition 28 to composition 30 than secretion 24, and FIG. 4 shows a formulation 36 including composition 28 but no composition 30. Formulations 34 and 36 may be described as being bio-matched but not bio-identical to a chemistry (or a composition) of secretion 24 (see FIG. 1).

Formulation 34 and/or formulation 36 may be useful for promoting the health of region 22 (see FIG. 1) and/or the desired effect of secretion 24. For example, composition 28 (or a characteristic of composition 28) may be identified as a significant contributor to the health of region 22 and/or to the desired effect of secretion 24. For example, a higher ratio of composition 28 to composition 30 may be identified as promoting the health of region 22, in which case formulation 34 and/or formulation 36 may be applied to region 22 (or to another body having a corresponding region deficient in composition 28) to increase a supply of composition 28 in that region.

Bio-matching a formulation to body 20 may involve "bio-balancing" the formulation to body 20. For example, ingredients (or compositions) that may be foreign to, produced by, or present in body 20 may be identified as possibly (or actually) detracting from (or harming) the health of region 22 (or body 20 as a whole). In this case, formulations 32, 34, and/or 36 may be bio-balanced by avoiding inclusion of one or more of these possibly or actually harmful ingredients (or compositions).

In some embodiments of bio-balancing a formulation to a vagina, harmful ingredients to avoid may include detergents and surface-active agents, glycerol (or glycerine) and other humectant/solvent excipients, one or more preservatives such as chlorhexidine and EDTA, salt in a concentration that makes the formulation not isotonic in the vagina, and/or acid in a concentration that does not match that of a healthy vagina.

Typically, portions (or regions) of male and female human bodies secrete various natural substances (or secretions). For example, a portion of a female human body or a male human body (e.g., a gland, organ, or flora associated with the portion or an organ) may secrete or produce one or more particular substances (e.g., lactic acid, saliva, etc.) for one or more particular functions (e.g., lubricating, moisturizing, cell protection, cell repair, protection from pathogens or foreign matter such as dust, etc.).

For example, the female body may include eyes secreting a first substance, a scalp secreting a second substance, ears secreting a third substance, nostrils secreting a fourth substance, a mouth secreting a fifth substance (e.g., saliva), lips of the mouth secreting a sixth substance, armpits secreting a seventh substance, nipples secreting an eighth substance (e.g., pheromones), an epidermis secreting a ninth substance, genitalia secreting a tenth substance (e.g., lactic acid produced by microflora living in the genitalia), a rectum secreting an eleventh substance, and feet secreting a twelfth substance.

The male body may include similar portions secreting (or producing) similar substances. However, due to differences between males and females (e.g., hormonal differences, genetic differences, among others) portions of the male body may differ from portions of the female body, and portions of the male body may secrete substances (e.g., pheromones) that are different than the substances secreted by the female body. For example, the male may include a penis and a scrotum secreting respective thirteenth and fourteenth substances, and a mouth of the male may secrete saliva having a composition that is different than a composition of saliva from the mouth of the female.

The genitalia (commonly referred to as a vagina) of the female human body may include labia majora, labia minora, a vagina, a cervix, a uterus, a urethra, a clitoris, a mons pubis, a symphysis pubis, and ovaries. Typically, the labia majora and the labia minor lead to the vagina, the cervix, and the uterus; and the urethra leads from the urinary bladder out of the female body through the labia minora and the labia majora.

A generally healthy vagina may include (or produce, or have present therein) various natural lubricants. For example, microflora (or bacteria) of the vagina (e.g., lactobacilli) may produce a first anti-microbial lubricant (e.g., lactic acid). Typically, microflora (e.g., vaginal bacteria) of a generally healthy vagina is dominated by *Lactobacillus crispatus*, which generally produce equal amounts of L-lactic acid and D-lactic acid. Further, a membrane of a vaginal wall of the vagina may produce a second lubricant (e.g., moisture), mucus glands of the cervix may secrete a third lubricant (e.g., different variations of mucus before and during ovulation), and glands, such as glandula vestibularis major located near an opening to the vagina, may secrete a fourth lubricant (e.g., a fluid such as mucus) when the female is sexually aroused.

In particular, mucus from the glands of the cervix and/or moisture from the vaginal wall membrane may provide lubrication within the vagina, and the fluid from the glandula vestibularis major may moisten the labial opening of the vagina, which may make contact with this area more comfortable for the female.

Typically, the female and/or a sexual partner of the female may apply an additional lubricant to components of the genitalia the female, such as the vagina and/or the labia majora and the labia minora, to increase lubrication of the vagina, which may enhance the sexual experience and/or prevent breakage of a condom. For example, the male 70 may roll a condom onto his penis, such that an inside portion of the condom is in contact with the penis. The male may then apply a personal lubricant, such as over the counter K-Y® jelly, to an outside portion of the condom. The female and the male may then engage in sexual intercourse, with the over the counter lubricant providing additional lubrication between the outside portion of the condom and the vagina. However, as previously described, pre-existing lubricants often include components (such as detergents like Nonoxynol-9) that are not bio-balanced to a healthy vaginal environment, and application of such components may make the vaginal environment more prone to disease or damage.

Accordingly, the applicant has discovered that formulating a composition (e.g., topical gel, cream, lubricant, etc.) to match a composition (e.g., chemical composition, and/or characteristics thereof) of a secretion of a selected region of a human body (e.g., a healthy vagina) may provide or enhance a desired effect (e.g., lubrication) and promote health.

For example, FIG. 5 shows a schematic representation of a female body 40. A vagina 60 of body 40 may secrete one or more substances (or secretions), as previously described. The one or more substances may include an identified secretion 80 having a composition 100. If vagina 60 (and/or body 40) is relatively or generally healthy, then composition 100 may include L-lactic acid 102 (i.e., L-enantiomers) and D-lactic acid 104 (D-enantiomers), which are the two optical isomers of lactic acid. For example, microflora of a generally healthy vagina typically produces lactic acid comprising approximately 50% L-lactic acid and 50% D-lactic acid (i.e., lactic acid having a racemic index of about 50% L/50% D). In contrast, it has been found that BV more commonly occurs in vaginas with microflora that produce a large percentage of L-lactic acid and produce only a small percentage (or no percentage) of D-lactic acid.

To provide improved lubrication and vaginal health, applicant has formulated a vaginal lubricant that substantially matches an actual composition and/or characteristic of healthy vaginal secretions and that avoid inclusion of harmful ingredients (e.g., detergents, surface-active agents, glycerol, chlorhexidine, and EDTA). The result is a formulation that is bio-matched (or bio-balanced) to healthy vaginal secretions. Such a bio-matched vaginal lubricant should not include (or avoid inclusion of) any ingredient that might injure healthy vaginal lactobacilli. Rather, the bio-matched vaginal lubricant may include one or more of the following components and/or characteristics (or properties) that are substantially matched to the components and/or characteristics (or properties) of a healthy vaginal secretions:

an aqueous gel component—for example, the bio-matched vaginal lubricant may include a gel that does not include glycerol or other solvents, but only water (or comprises mainly water), as is true for mucus secretions of a healthy vagina;

one or more viscoelastic properties—for example, the bio-matched vaginal lubricant may use a safe and natural polymer to create a gel with viscoelastic properties that match those of vaginal secretions (e.g., mucus) of a healthy vagina, which may include not only matching a viscosity of the vaginal secretions at a given shear rate, but also across a broad range of shear rates—more specifically, mucus of the vagina is a "shear-thinning" lubricant (e.g., a gel that becomes very slippery, and has a low viscosity when the gel is being sheared, as in the act of intercourse), and matching the viscoelastic properties of the vaginal lubricant to the mucus of the vagina may provide for the gel of the bio-matched vaginal lubricant not dripping out of the vagina, but remaining in the vagina and becoming very slippery with a low viscosity only when being sheared;

an isotonic property—for example, the bio-matched vaginal lubricant may be formulated to have a salt composition that makes the bio-matched vaginal lubricant isotonic in the vagina (e.g., when the bio-matched vaginal lubricant is in the vagina, the bio-matched vaginal lubricant will not cause water to be secreted into the vagina, nor cause water to be absorbed out of the vagina);

an isotonic property that matches as close as possible the salts present in a vaginal secretion (the salts in a vaginal secretion include sodium, potassium, calcium, and magnesium).

a pH property—for example, the pH of the bio-matched vaginal lubricant may be formulated to closely match the pH of a healthy vagina (i.e., pH 3.5±0.3%);

a lactic acid component—for example, the bio-matched vaginal lubricant may be acidified with ~1±0.5% lactic acid, which is a concentration that may match that of a healthy vagina; and a racemic lactic acid component—for example, the bio-matched vaginal lubricant may include lactic acid that is an essentially racemic (equal) mix of the two optical isomers of lactic acid (i.e., the D- and L-isomers) to match the mixture of these isomers in a healthy vagina—more specifically, a healthy vagina is typically acidified by lactobacilli that produce both D- and L-isomers of lactic acid, but only a minority of women have these healthy, protective lactobacilli, and most other women either have few if any lactobacilli or have strains of lactobacilli that fail to make the D-isomer, and thus the bio-matched vaginal lubricant may be formulated to healthy vaginal secretions by including an approximately even mix of the two isomers (i.e., a racemic mix of D- and L-isomers of lactic acid).

With respect to achieving the desired biomatching property recited above, applicant has learned it is particularly important to biomatch iso-osmolality, pH, and 1% by weight racemic acid. The isotonic property recited above involves a salt composition that is isotonic with vaginal fluid. Isotonicity can be achieved with variations in sodium, and potassium chlorides as well as with other osmotically active compounds.

Osmolality of healthy vaginal secretions has been measured, and using that measurement, the invention includes a gel that biomatches osmolality to that of a healthy vagina. Based upon that biomatching, the invented lubricant, including a gel version, is as close to being isotonic as is possible. Biomatching, that is, matching the osmolality of vaginal secretions is the best way to achieve isotonicity, given the absence of any direct observations of fluid movement into or out of the vagina. The invented lubricant is isotonic, that is, for example, the gel version is effective to lubricate a human vagina that is neither: (i) hypertonic (causes the vaginal epithelium to secrete fluid that dilutes the lubricant which can cause toxicity in the vagina), nor (ii) hypotonic (causes fluid to be withdrawn from the vagina and drying it).

Further, the applicant has found that formulating a vaginal lubricant to match the vaginal acidity of a healthy vagina, particularly by including lactic acid in the formulation, and more specifically by including lactic acid that is substantially racemic, kills HIV and many other pathogens.

Accordingly, FIG. 6 shows a first formulation 106 that is bio-matched to a chemistry of body 40 of FIG. 5 (e.g., to a chemistry of secretion 80 of vagina 60). For example, FIG. 6 shows formulation 106 including 50% L/50% D racemic lactic acid. In some embodiments, formulation 106 may include lactic acid having a racemic index of about 10% L/90% D. In some embodiments, formulation 106 may include lactic acid having a racemic index of about 20% L/80% D. In some embodiments, formulation 106 may include lactic acid having a racemic index of about 30% L/70% D. In some embodiments, formulation 106 may include lactic acid having a racemic index of about 40% L/60% D. In some embodiments, formulation 106 may include lactic acid having a racemic index of about 60% L/40% D. In some embodiments, formulation 106 may include lactic acid having a racemic index of about 70% L/30% D. In some embodiments, formulation 106 may include lactic acid having a racemic index of about 80% L/20% D. In some embodiments, formulation 106 may include lactic acid having a racemic index of about 90% L/10% D. In some embodiments, formulation 106 may include D-lactic acid, and no L-lactic acid.

In some embodiments, the racemic lactic acid (or lactic acid having another suitable racemic index) may comprise about 1% of formulation 106. For example, the racemic lactic acid may comprise about 0.5% to about 1.5% of formulation 106. In other embodiments, the racemic lactic acid (or lactic acid having another suitable racemic index) may comprise other suitable percentages of formulation 106. In some embodiments, the racemic lactic acid may be synthetically-derived. In other embodiments, the racemic lactic acid may be naturally-derived. Applying formulation 106 to vagina 60 may lubricate vagina 60, and may promote the health of vagina 60.

FIGS. 7 and 8 show respective formulations 108 and 110, which may be considered as bio-matched to composition 100 of secretion 80 of FIG. 5. For example, FIG. 7 shows formulation 108 including lactic acid having a racemic index of 30% L/70% D, which may be suitable for application to a vagina that is slightly deficient in D-lactic acid. FIG. 8 shows formulation 110 including D-lactic acid, but no L-lactic acid, which may be suitable for application to a vagina that has a greater deficiency of D-lactic acid (or does not produce any D-lactic acid at all).

Figure 9:
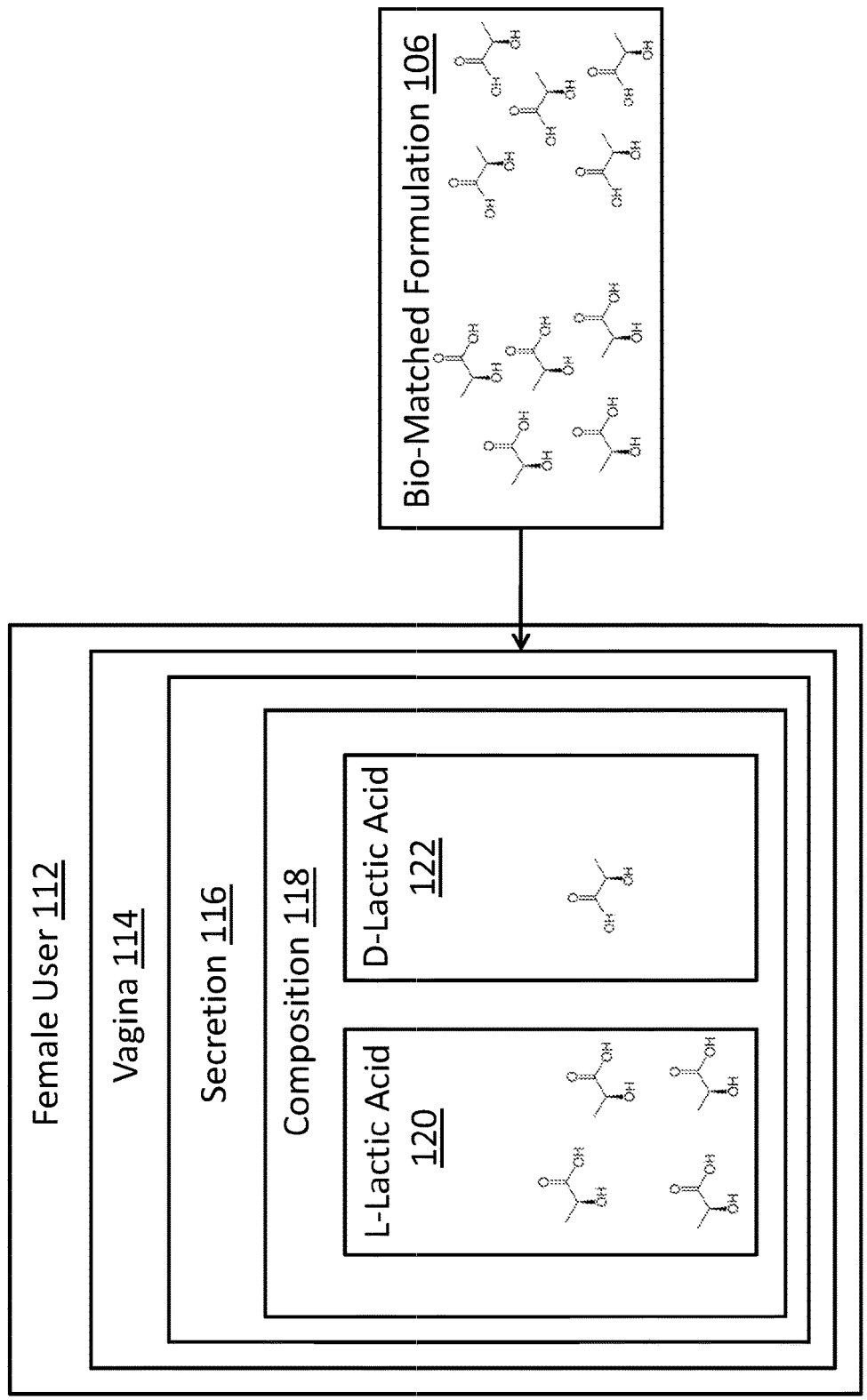
FIG. 9 is a block diagram schematically depicting the bio-matched formulation of FIG. 6 being applied to an unhealthy vagina of a female user.
Figure 10:
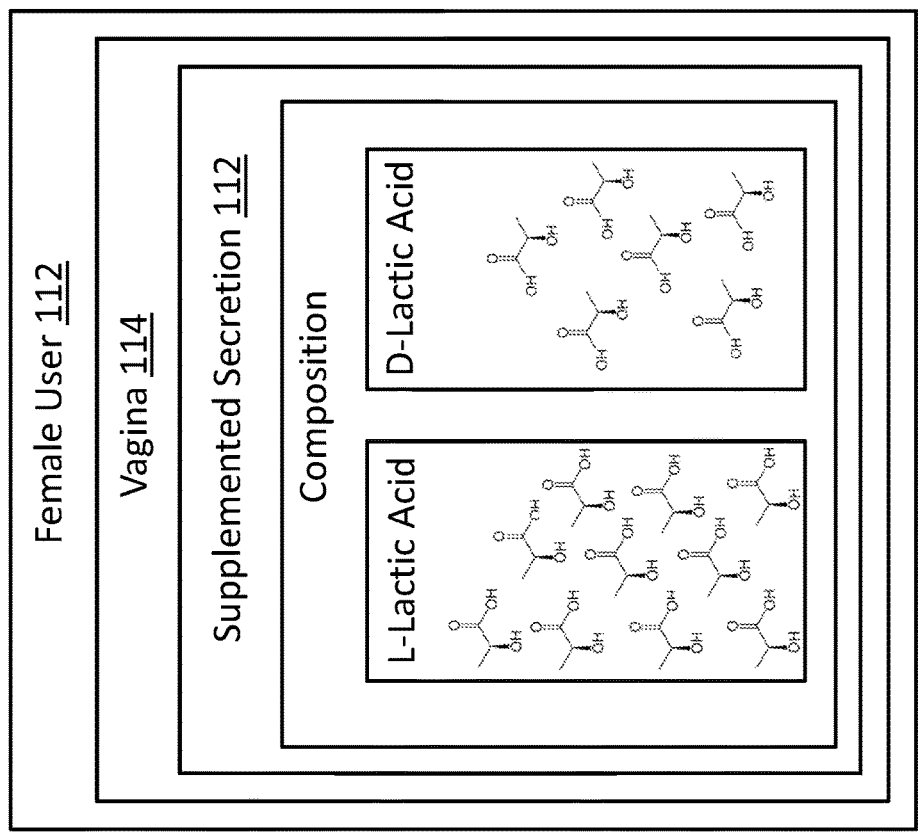
FIG. 10 is a block diagram of the female user of FIG. 9 after application of the bio-matched formulation.

FIG. 9 shows a schematic representation of a female user 112 having a vagina 114 that produces a secretion 116. Secretion 116 may include a composition 118, which may comprise lactic acid including L-lactic acid 120 and D-lactic acid 122. As shown, the lactic acid of secretion 116 has a racemic index of 80% L/20% D, which may be associated with a generally unhealthy condition of vagina 114 (or a condition prone to disease). Application of formulation 106 to vagina 114 may both lubricate vagina 114 and promote the health of vagina 114 (and female user 112). For example, formulation 106 may be added to secretion 116 to produce a supplemented secretion 124 (see FIG. 13).

FIG. 13 shows a schematic representation of female user 112 after application of formulation 106 (see FIG. 12) to vagina 114. As shown, supplemented secretion 124 of vagina 102 includes lactic acid having a racemic index of about 62.5% L/37.5% D, which may more closely match the lactic acid produced by microflora of a healthy vagina.

FIG. 14 shows an exemplary method, generally indicated at 200, of bio-matching a topical gel (or cream, lubricant, or other suitable substance) to a living body.

Method 200 may include a step 202 of selecting a region of the body. Step 202 may involve selecting a region including one or more components, such one or more glands, one or more organs, and/or flora (e.g., microflora including bacteria) that secrete various substances. For example, these components may secrete one or more particular substances (e.g., lactic acid, saliva, etc.) for one or more particular functions (e.g., lubricating, moisturizing, cell protection, cell repair, excretion of waste, protection from pathogens or foreign matter such as dust, etc.). The selected body may be a human body, and the selected region may be a vagina.

Method 200 may include a step 204 of identifying a secretion of the selected region. Step 204 may involve selecting a secretion produced by (or present in) a generally healthy region, such as a generally healthy vagina.

Step 204 may involve identifying a secretion that a relatively healthy body (or part thereof) produces. For example, microflora of a generally healthy vagina typically produces lactic acid comprising approximately 50% L-lactic acid (i.e., L-enantiomers) and 50% D-lactic acid (i.e., D-enantiomers). In contrast, as previously described, BV more commonly occurs in vaginas with microflora that produce lactic acid with little or no percentage of D-lactic acid. Accordingly, step 204 may involve identifying lactic acid having L-enantiomers and D-enantiomers.

Method 200 may include a step 206 of identifying a composition (e.g., chemical composition, molecular composition, ionic composition, or characteristics or properties thereof) of the identified secretion. Step 206 may involve identifying lactic acid. Step 206 may involve identifying lactic acid having a racemic index in a range of about 50% L/50% D.

Method 200 may include a step 208 of formulating the topical gel to (substantially) match the identified composition of the identified secretion. Step 208 may involve selecting lactic acid that is approximately racemic. Step 208 may involve selecting synthetic acid. Step 208 may involve selecting racemic synthetic acid. Step 208 may involve selecting pure racemic synthetic acid having a racemic index of 50% L/50% D. Step 208 may involve formulating the topical gel to include about 1% lactic acid (synthetic and/or racemic). In some embodiments, step 208 may involve bio-balancing the topical gel to avoid (or by avoiding) inclusion of one or more ingredients that are toxic (or harmful) to microbiota of the generally healthy vagina (or any vagina). Examples of ingredients that are toxic (or harmful) to the microbiota of a vagina include detergents, surface-active agents, glycerol, many types of preservatives including chloride and EDTA, salt concentrations/formulations that make the formulation non-isotonic in the vagina, and acid/base concentrations/formulations that do not match the pH of the generally healthy vagina.

Method 200 may further comprise applying the topical gel to the selected region of the human body (or a region of another human body corresponding to the selected region). For example, method 200 may further comprise applying the topical gel to a vagina. For example, applying the topical gel may involve rolling a condom onto a penis, such that an inner surface of the condom contacts the penis; disposing the topical gel onto an outer surface of the condom; and bringing the vagina into contact with the outer surface of the condom.

In some embodiments, the topical gel may be disposed on the condom prior to the condom being rolled onto the penis. For example, the topical gel may be disposed on the condom (e.g., the outer and/or inner surface) during a manufacturing and/or packaging step of the condom.

In other embodiments, the topical gel may be provided in a package or tube that is separate from a package containing a condom. For example, the topical gel may be provided in a stand-alone container. The user may open the container and apply the topical gel directly to the vagina, directly to the penis, and/or to any suitable surface of a condom.

In some embodiments, method 200 may further comprise applying the topical gel to a suitable medical device. For example, the topical gel may be suitable for lubricating one or more implements used during a pelvic exam, such as an outer surface of a glove disposed on a hand of a gynecologist.

EXAMPLE 1

The following is to prepare a vaginal lubricant according to a first version of the invention, with percentages by weight of the total formulation shown parenthetically after each component. Certified organic aloe vera powder (95%), commercially available under the trademark SD 200X™, is hydrated in a separate mixing tank. Agar (0.2%) is added to hydrated aloe vera powder, and the mixture is pasteurized by heating it to 160 degrees F. for about thirty (30) minutes. After allowing the mixture to cool to about 115 degrees F., Xanthan gum (3.1%) is added. The following inorganic ingredients are combined in a separate mixing container potassium sorbate (0.25%), sodium benzonate (0.20%) and natural flavor (0.35%). After being suitably mixed, the inorganic ingredients are added to the aloe vera mixture. Lactic acid (0.9%) is suitably mixed into the aloe vera mixture to match to the desired pH of vaginal secretions. The resulting mixture is tested at completion and prior to dispensing into commercial containers for microbial count. Microbial count is tested by using commercially recognized bacterial challenge tests, to meet the standard of no more than ten colony forming units (CFUs) present. Other quality control tests are performed, including commercially known 30-day shelf/oven testing, and freeze/thaw testing.

EXAMPLE 2

The following is to prepare a vaginal lubricant according to a second version of the invention, with percentages by weight of the total formulation shown parenthetically after each component. Certified organic aloe vera powder (95%), commercially available under the trademark SD 200X™, is hydrated in a separate mixing tank. Agar (0.2%) is added to hydrated aloe vera powder, and the mixture is pasteurized by heating it to 160 degrees F. for about thirty (30) minutes. After allowing the mixture to cool to about 115 degrees F., Xanthan gum (3%) is added. The following inorganic ingredients are combined in a separate mixing container potassium sorbate (0.25%), sodium benzonate (0.20%) and natural flavor (0.35%). After being suitably mixed, the inorganic ingredients are added to the aloe vera mixture. Racemic lactic acid (1%) is suitably mixed into the aloe vera mixture to bring the pH of that mixture within the range of 3.5-3.9. Microbial count is tested by using commercially recognized bacterial challenge tests, to meet the standard of no more than ten colony forming units (CFUs) present. Other quality control tests are performed, including commercially known 30-day shelf/oven testing, and freeze/thaw testing.

EXAMPLE 3

The following is to prepare a vaginal lubricant according to a third version of the invention, following a procedure as described in connection with Examples 1 and 2, and with percentages by weight of the total formulation shown parenthetically after each component.

| Component | Percentage by weight | Function |
| --- | --- | --- |
| Water | 94.5-97.5% | Solvent |
| Hydroxyethylcellulose | 0.5-1.5% | Viscosity modifier |
| Carrageenan | 0.25-.90% | Binder |
| Ceratonia Siliqua (Carob) Gum | 0.07-.30% | Binder |
| Xanthan Gum | 0.07-.30% | Binder |
| Sodium Chloride | 0.25-.70% | Osmolality modifier |
| Lactic Acid | 0.5-1.5% | pH adjuster |
| Sodium Hydroxide | 0.07-.30% | pH adjuster |
| Potassium Sorbate | 0.15-.4% | Preservative |
| Sodium Benzoate | 0.15-.4% | Preservative |
| Calcium Chloride | 0.005-.02% | Viscosity modifier |

According to recently published test results, healthy vaginal secretions have an osmolality of 370+/−10 mOsm/Kg, which is higher than the osmolality of most other bodily fluids, which is about 290+/−10 mOsm/Kg. The osmolality of this above-identified version of the invention is 350+/−10 mOsm/Kg.

The primary gelling agent in the third version is HEC (hydroxyethylcellulose), and the secondary gelling agent is Carrageenan, a nontoxic material made from seaweed. Utilizing Carrageenan causes the third version to have the added feature of tending to minimize HSV and HPV infections. The primary salt ions used in the third version are Na, K, Cl, and Ca, and that same combination is found in the vagina. While the concentrations of those four salts are not identical to those in a healthy vagina, the combination of those four salts have been adjusted such that this third version has an osmolality that matches the osmolality of health vaginal secretions.

The following paragraphs may provide further information regarding embodiments of the present disclosure.

A. A method of bio-matching a topical gel, the method comprising: selecting a region of a living body, wherein selecting the region involves selecting a vagina; identifying a secretion of the selected vagina; identifying a composition of the identified secretion; and formulating the topical gel to match the identified composition of the identified secretion.

A1. The method of paragraph A, wherein the body is a human body.

A2. The method of paragraph A, wherein identifying the secretion involves identifying a secretion present in a generally healthy vagina.

A3. The method of paragraph A2, wherein identifying the composition of the identified healthy secretion involves identifying lactic acid.

A4. The method of paragraph A3, wherein identifying lactic acid involves identifying racemic lactic acid having a racemic index in a range of about 50% L/50% D.

A6. The method of paragraph A5, wherein selecting lactic acid involves choosing an approximately racemic mixture with between 30% to 70% L and between 70% to 30% D.

A7. The method of paragraph A6, wherein formulating the topical gel involves formulating the topical gel to include about 1% of the selected lactic acid.

A8. The method of paragraph A2, wherein formulating the topical gel involves bio-balancing the topical gel by avoiding inclusion of one or more ingredients that are toxic to microbiota of the generally healthy vagina.

B. A topical gel for human use, the gel comprising: a formulation matched to a chemistry of a particular part of a human body, the formulation including lactic acid.

B1. The gel of paragraph B, wherein the particular part of the human body is a vagina.

B2. The gel of paragraph 81, wherein the chemistry is a generally healthy chemistry associated with the vagina.

B3. The gel of paragraph B2, wherein the generally healthy chemistry includes lactic acid having a racemic index of about 50% L/50% D.

B4. The gel of paragraph B3, wherein the formulation comprises approximately 1% lactic acid having a racemic index in a range of about 30% L/70% D to 70% L/30% D.

B5. The gel of paragraph B4, wherein the racemic index of the 1% lactic acid is approximately 50% L/50% D.

C. A topical gel for human use, the gel comprising: a formulation matched to a chemistry of a particular part of a human body, the formulation including lactic acid having a racemic index in a range of about 50% L/50% D.

C1. The gel of paragraph C, wherein the particular part is a vagina.

C2. The gel of paragraph C1, wherein the chemistry corresponds to a generally healthy chemistry associated with flora of the vagina.

C3. The gel of paragraph C2, wherein the generally healthy chemistry includes racemic lactic acid having a racemic index of about 50% L/50% D.

C4. The gel of paragraph C3, the lactic acid of the formulation comprises about 1% of the formulation.

D. A vaginal lubricant, comprising: a formulation including lactic acid having a racemic index that is bio-matched but not bio-identical to a racemic index of natural lubricants in a healthy vagina.

D1. The lubricant of paragraph D, wherein the lactic acid of the formulation is naturally-derived.

D2. The lubricant of paragraph D, wherein the lactic acid of the formulation is synthetically-derived.

D3. The lubricant of paragraph D, wherein the racemic index of the lactic acid of the formulation is in a range of about 30% L/70% D to 70% L/30% D, and the racemic index of the natural lubricants is about 50% L/50% D.

D4. The lubricant of paragraph D3, wherein the lactic acid of the formulation is synthetic lactic acid comprising about 1% of the formulation, the synthetic lactic acid having a racemic index of about 50% L/50% D.

D5. The lubricant of paragraph D, wherein vagina bacteria of the healthy vagina is dominated by *Lactobacillus crispatus* which produce lactic acid that is included in the natural lubricants, the lactic acid of the natural lubricants having a racemic index of approximately 50% L/50% D.

D6. The lubricant of paragraph D5, wherein the lactic acid of the formulation has a racemic index in a range of 80% L/20% D to 20% L/80% D, thereby resulting in the formulation being bio-matched to the natural lubricants of the healthy vagina.

The disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. Each example defines an embodiment disclosed in the foregoing disclosure, but any one example does not necessarily encompass all features or combinations that may be eventually claimed. Where the description recites "a" or "a first" element or the equivalent thereof, such description includes one or more such elements, neither requiring nor excluding two or more such elements. Further, ordinal indicators, such as first, second or third, for identified elements are used to distinguish between the elements, and do not indicate a required or limited number of such elements, and do not indicate a particular position or order of such elements unless otherwise specifically stated.

What is claimed is:

1. A topical gel for human use, the gel comprising:
 a formulation matched to a composition of a particular part of a human body, the formulation being isotonic, and including lactic acid that has a racemic index.

2. The gel of claim 1, wherein the particular part of the human body is a vagina.

3. The gel of claim 2, wherein the composition is a generally healthy composition associated with the vagina, and wherein the osmolality of the gel is in the range of about 340-380 mOsm/Kg.

4. The gel of claim 3, wherein the generally healthy composition includes lactic acid having a racemic index of about 50% L/50% D.

5. The gel of claim 4, wherein the formulation comprises approximately 1% lactic acid having a racemic index in a range of about 30% L/70% D to about 70% L/30% D.

6. The gel of claim 5, wherein the racemic index of the 1% lactic acid is approximately 50% L/50% D, and wherein the osmolality of the gel is in the range of about 340-380 mOsm/Kg.

7. An isotonic vaginal lubricant, comprising:
 a formulation including lactic acid having a racemic index that is bio-matched but not bio-identical to a racemic index of natural lubricants in a healthy vagina.

8. The lubricant of claim 7, wherein vagina bacteria of the healthy vagina is dominated by *Lactobacillus crispatus* which produce lactic acid that is included in the natural lubricants, and wherein the lactic acid of the natural lubricants has a racemic index of approximately 50% L/50% D.

9. The lubricant of claim 8, wherein the lactic acid of the formulation has a racemic index in a range of 80% L/20% D to 20% L/80% D, thereby resulting in the formulation being bio-matched to the natural lubricants of the healthy vagina.

10. A topical isotonic gel lubricant for application to a human vagina that has vaginal secretions and cells, the lubricant comprising:
   an aqueous isotonic gel formed substantially of water, lactic acid and plural salts, with the salts chosen to match those present in the vaginal secretions and, thereby, make the lubricant isotonic with respect to the vagina; and
   wherein the osmolality of the lubricant is in the range of about 290-440 mOsm/Kg.

11. The lubricant of claim 10, wherein the osmolality is in the range of about 330-400 mOsm/Kg.

12. The lubricant of claim 10, wherein the osmolality is in the range of about 350-380 mOsm/Kg.

13. The lubricant of claim 10, wherein the lactic acid has a isomer index in a range of about 50% L/50% D and being present at a concentration of 1±0.5% by weight.

14. The lubricant of claim 10, wherein the lubricant is formulated to have a pH in the range of 3.5±0.5%.

15. The lubricant of claim 10, wherein the gel is isotonic because it is effective to lubricate the human vagina in such a way to cause the vagina to be neither hypertonic nor hypotonic.

16. The lubricant of claim 10, wherein the isotonic gel tends to minimize HSV and HPV infections.

* * * * *